(12) United States Patent
Zhao et al.

(10) Patent No.: US 7,323,339 B2
(45) Date of Patent: Jan. 29, 2008

(54) MAIZE BZIP TRANSCRIPTION FACTORS AND GENES ENCODING THE SAME AND USE THEREOF

(75) Inventors: Jun Zhao, Beijing (CN); Lei Wang, Beijing (CN); Yunliu Fan, Beijing (CN)

(73) Assignee: The Institute of Biotechnology of the Chinese Academy of Agricultural Sciences, Beijing (CN)

( * ) Notice: Subject to any disclaimer, the term of this patent is extended or adjusted under 35 U.S.C. 154(b) by 43 days.

(21) Appl. No.: 11/046,255

(22) Filed: Jan. 28, 2005

(65) Prior Publication Data

US 2006/0021091 A1   Jan. 26, 2006

(51) Int. Cl.
*A01N 5/00* (2006.01)
*C12N 15/82* (2006.01)
*C12N 15/87* (2006.01)
*C12N 5/14* (2006.01)
*C07H 21/00* (2006.01)

(52) U.S. Cl. .................. 435/468; 435/320.1; 536/23.6; 800/278; 800/289

(58) Field of Classification Search .................... None
See application file for complete search history.

(56) References Cited

U.S. PATENT DOCUMENTS

2004/0072159 A1   4/2004   Takaiwa et al.

FOREIGN PATENT DOCUMENTS

EP   1 209 232   5/2002
WO   WO 01/14559   3/2001
WO   WO 2004/011493   2/2004

OTHER PUBLICATIONS

Siberil et al. (Eur. J. Biochem., 268:5655-5666, 2001).*
Cowell et al. (Mol. Cell Biol., 12:3070-3077, 1992).*
Guo et al. (PNAS, 101:9205-9210, 2004).*
Keskin et al. (Protein Science, 13:1043-1055, 2004).*
Thornton et al. (Nature structural Biology, structural genomics supplement, Nov. 2000), 991-994.*
Finkelstein et al. (The Plant Cell, 12:599-609, 2000).*
Foster, R. et al.; "Plant bZIP proteins gather at ACGT elements"; Laboratory of Plant Molecular Biology, The Rockefeller University, New York, NY; pp. 192-200.
Jakoby, M. et al.; "bZIP transcription factors in *Arabidopsis*"; Trends in Plant Science; vol. 7, No. 3; Mar. 2002; pp. 106-111.
Nambara, E. et al.; "A Screen for Genes That Function in Abscisic Acid Signaling in *Arabidopsis thaliana*"; Genetics 161; pp. 1247-1255.

* cited by examiner

*Primary Examiner*—Phuong Bui
*Assistant Examiner*—Vinod Kumar
(74) *Attorney, Agent, or Firm*—Scully, Scott, Murphy & Presser, P.C.

(57) ABSTRACT

The invention discloses maize bZIP transcriptional factors, namely, ABP2, ABP4 and ABP9, the genes encoding these factors, and the use thereof. The transcriptional factors are proteins having an amino acid sequence set forth in SEQ ID NO: 2, 4, or 6, or proteins derived therefrom by substitution, deletion or addition of one or more amino acid residues of SEQ ID NO: 2, 4, or 6, and having the same activity as a protein shown by SEQ ID NO: 2, 4, or 6. The ABP2, ABP4 and ABP9 genes encoding these factors, respectively, are the DNA sequences having an identity of more than 90% with a sequence shown by SEQ ID NO: 1, 3 or 5 and the encoded proteins having such same functions. These genes are important for breeding plant varieties with an enhanced tolerance to abiotic stresses and for improving plant tolerance to abiotic stresses.

10 Claims, 4 Drawing Sheets

(4 of 4 Drawing Sheet(s) Filed in Color)

MAIZE BZIP TRANSCRIPTION FACTORS AND GENES ENCODING THE SAME AND USE THEREOF

CROSS-REFERENCE TO RELATED APPLICATIONS

This application claims the benefit of PCT/CN03/00599 filed Jul. 28, 2003 and Chinese Patent Application No. 02127187.9 filed Jul. 30, 2002. The disclosures of the above applications are incorporated herein by reference.

FIELD OF THE INVENTION

The present invention relates to transcription factors, genes encoding the transcription factors, and the use of such transcription factors and genes in the field of plant genetic engineering. More especially, the invention relates to maize bZIP transcription factors, genes encoding maize bZIP transcription factors, the use of such bZIP transcription factors and genes.

BACKGROUND OF THE INVENTION

Upon exposure to abiotic stresses such as drought, high salinity, low temperature and etc., plant will not simply passively endure the stressful conditions. In stead, plant will actively cope with the environmental stresses through eliciting responses of its in-built defense system, including, e.g., biosynthesis of new proteins, changes in metabolism, accumulation of stress-tolerant chemicals, and so on (Hans J. Plant cell. 1995, 7: 1099-1111). Many proteins are involved in plant response to abiotic stresses (Ashwani Pareek. Current Science. 1998, 75: 1170-1174) and they act coordinatively to enhance tolerance by modulating biochemical, metabolic and physiological adaptions. Studies have shown that enhancing the expression of single effector protein genes was not able to significantly improve plant performance under stress conditions.

Under abiotic stress conditions, many proteins induced in plant are involved in tolerance to abiotic stresses. The genes encoding some of the proteins have been cloned (Anil Grover. Current Science. 1998, 75: 689-695). In efforts to increase plant tolerance to abiotic stresses, such as cold, drought and salt, many stress-related genes from various sources have been cloned and transformed into different plant species (Shavindra Bajaj. Molecular Breeding. 1999, 5: 493-503). The proteins encoded by those cloned genes can be classified into three groups: 1) Enzymes involved in the synthesis of osmolyte. For example, the introduction of gene mtlD derived from *E. coli* into tobacco increased the content of mannitol in the crop. Transgenic tobacco or rice over-expressing P5CS gene elevated its content of proline. The introduction of codA gene into arabidopsis or rice increased the content of glycine betaine in transgenic plants (Sakamoto A. PMB. 1998, 38: 1011-1019). 2) Late Embryogenesis Abundant (LEA) and related proteins. For example, constitutive expression of cor15a gene in arabidopsis discouraged the formation of freeze-induced harmful membrane structures (Steponkus PL. PNAS. 1998, 95: 14570-14575). 3) Proteins related to oxidative stress. For example, over-expressing of Mn-SOD gene in alfalfa (Mckersic BD. Plant Physiol. 1996, 111: 1177-1181) and of GST gene in tobacco increased tolerance to stresses. However, although the expression of single effector genes in transgenic plants can enhance an aspect of plant stress responses under experimental conditions, the overall performance of the transgenic plants under stresses was not largely improved. Recently, the gene encoding an tolerance-related transcription factor CBF1 (C-repeat Binding Factor) was over-expressed in arabidopsis and showed that CBF1 enhanced the expression of a series of cold-related effector genes. Moreover, Compared with the above described plants over-expressing single effector genes, the enhanced expression of CBF1 significantly improved the cold tolerance in transgenic arabidopsis plants (Kirsten R. Science. 1998, 280: 104-106). Similarly, over expression of transcription factor DREB1A gene in arabidopsis induced multiple stress-related genes and largely increased plant tolerance to salt, cold and drought stresses (Mie Kasuga. Nature Biotechnology. 1999, 17: 287-291).

Studies show that plants produce a large amount of reactive oxygen species (ROS) under stress conditions such as drought, salinity and low temperature, leading to oxidative stress. (Zhu J K. Trends Plant Sci. 2001, 6: 66-71). Because ROS are highly active, they can lead to serious damages to cells, for example, membrane peroxidation, inactivation of key enzymes, DNA lesions and etc. Therefore, the scavenging of excess ROS is critical for plants to increase tolerance to abiotic stresses. Catalase (e.g., CAT1) plays an important role in the scavenging of ROS. However, under stress conditions, the plant's ability for induction of its endogenous anti-oxidant system is poor, which limits the further increase of plant tolerance. Therefore, the cloning of genes encoding the transcription factors that regulate the expression of Cat1 will not only further our understanding on ROS signal tranduction pathway, but provide strategies for generating new crop varieties with enhanced tolerance to stresses such as drought, salt, cold and etc. This is because such trans-acting factor can regulate the expression of anti-oxidant genes including Cat1, as well as other stress-responsive genes.

ABRE is an ABA (abscisic acid) responsive element located in the promoter region of many stress responsive genes, which is characterized by (C/G/T)ACGTG(G/T)(A/C) (SEQ ID NO: 31 sequence (Chen WQ. Plant Cell. 2001, 14: 559-574). The promoter region of Cat1 contains two ABRE-like DNA sequence, namely ABRE1 and ABRE2. Deletion analysis shows that ABRE2 (5'-GAAGTC-CACGTGGAGGTGG) (SEQ ID NO: 7) is the cis-element necessary for the regulation of Cat1 by ABA. The expression of Cat1 increases along with the elevation of ABA content during maize embryogenesis, a process in which seeds accumulate nutrients and undergo deccicated as well as induction of tolerance to dehydration. Previous study showed that there existed trans-acting factors interacting with ABRE2 in cells during maize embrogenesis. The trans-acting factors can be classified into two groups, one is ABA-dependent (namely Cat1 promoter Binding Factor 1, CBF1), and the other is ABA-independent (namely Cat1 promoter Binding Factor 2, CBF2) (Lingqing M. Guan, The Plant Journal. 2000, 22(2): 87-95). These transcription factors have not been cloned up to now.

SUMMARY OF INVENTION

The object of the present invention is to provide maize bZIP transcription factors and the encoding genes thereof.

The maize bZIP transcription factors provided by the invention are isolated from maize and named as ABRE Binding Proteins ABP2, ABP4 and ABP9, respectively. They are the proteins having the amino acid sequence shown by SEQ ID NO 2, 4 or 6 in the sequence listing, or the proteins derived from the sequence shown by SEQ ID NO 2, 4 or 6, by substitution, deletion or addition of one or more amino acid residues, and with the same activity to the proteins of the amino acid sequence shown by SEQ ID NO 2, 4 or 6.

ABP2 represents the protein having the amino acid sequence shown by SEQ ID NO 2 in the sequence listing and comprising 351 amino acid residues.

ABP4 represents the protein having the amino acid sequence shown by SEQ ID NO 4 in the sequence listing and comprising 360 amino acid residues.

ABP9 represents the protein having the amino acid residue sequence shown by SEQ ID NO 6 in the sequence listing and comprising 385 amino acid residues.

A BLAST analysis is performed by inputing the protein sequences of ABP2, ABP4 and ABP9 of the invention into GenBank. The result shows that ABP2, ABP4 and ABP9 belong to the family of bZIP transcription factors. Compared with the reported bZIP transcription factors, ABP2, ABP4 and ABP9 each has low homology in amino acid sequence with the known factors.

The invention constructs a cDNA library with maize embryos of 17 days post pollination (17 dpp), using Not I adapter: 5'-pGACTAGTTCTAGATCGCGAGCGGC-CGCCC(T)$_{15}$ (SEQ ID NO: 8)-3' as a primer. And the capacity of the constructed cDNA library is $5.2 \times 10^6$ cfu.

The invention designs and synthesizes the following primers:

Primers for Reverse-transcription:

```
                                         (SEQ ID NO: 9)
ABP2 rv2: 5'-GCG ACA GCG ACG ACA GAT CA-3'

(SEQ ID NO: 10)
ABP4 rv2: 5'-AGC GCC AGA AGC GGA GGC CA-3'

(SEQ ID NO: 11)
ABP9 rv2: 5'-CCT TCA CCA GGA AGT CCT CCA-3'
```

Primers for PCR:

```
                                         (SEQ ID NO: 12)
AUAP fw:   5'-GGC CAC GCG TCG ACT AGT AC-3'

(SEQ ID NO: 13)
ABP2 rv3:  5'-AGG AAC TCC TCC AGA GTC AT-3'

(SEQ ID NO: 14)
ABP4 rv3:  5'-TCG TCG AAC GTC AAC GAG TAG-3'

(SEQ ID NO: 15)
ABP9 rv3:  5'-AAC CAA TCC TCC GTT CTC ACC-3'
```

By using the methods of reverse transcriptase-polymerase chain reaction (RT-PCR) and RACE, the invention clones the genes encoding maize bZIP transcription factors from maize embryos. The genes ABP2, ABP4 and ABP9 which respectively encode maize bZIP transcription factors ABP2, ABP4 and ABP9 are the DNA sequences sharing at least 90% homology to the DNA sequences defined by SEQ ID NO: 1, 3 and 5 respectively in the sequence listing, and accordingly encoding proteins with the same functions. ABP2 gene represents the DNA sequence shown by SEQ ID NO: 1 in the sequence listing, consisting of 1485 bp. The open reading frame of the gene is the DNA sequence from 114 to 1056 bases, beginning at the 5' end. ABP4 gene represents the DNA sequence shown by SEQ ID NO: 3 in the sequence listing, consisting of 1835 bp. The open reading frame of the gene is the DNA sequence from 93 to 1175 bases, beginning at the 5' end. ABP9 gene is the DNA sequence shown by SEQ ID NO: 5 in the sequence listing, consisting of 1510 bp. The open reading frame of the gene is the DNA sequence from 45 to 1202 bases, beginning at the 5' end.

By constructing each of the cloned genes of ABP2, ABP4 and ABP9 into the yeast expression vector pPC86, the invention studies the in vivo binding specificity of proteins ABP2, ABP4 and ABP9 with ABRE. The result shows that the products of the genes ABP2, ABP4, and ABP9 all have ABRE-binding specificity in yeast cells. By constructing each of the cloned genes of ABP2, ABP4 and ABP9 into the prokaryote expression vector pGEX4T-1, the invention studies the in vitro binding specificity of ABP2, ABP4 and ABP9 with ABRE. The result shows that the products of the genes ABP2, ABP4 and ABP9 all have ABRE-binding specificity in vitro and can specifically bind to the ABRE cis-element that contains core sequence of (C/G/T) ACGTG (G/T) (A/C).

By constructing the cloned genes of ABP2, ABP4 and ABP9 respectively into the yeast expression vector YepGAP and plant expression vector pBI121, the invention studies the in vivo binding specificity of ABP2, ABP4 and ABP9 to ABRE and the transcriptional activation function thereof in yeast and maize cells. The result shows that each of the products of the genes ABP2, ABP4, and ABP9 has ABRE-binding specificity in yeast cells and suspended maize cells. The result also shows that the products of those genes have the function of transcriptional activation. Thus, the products of the genes ABP2, ABP4, and ABP9 are transcription factors that have the ABRE binding specificity and the transcriptional activation function. In addition, the genes ABP2, ABP4, and ABP9 can be expressed through the induction of stress conditions such as salt, drought, hydrogen peroxide, ABA and etc.

The genes ABP2, ABP4, and ABP9 are respectively constructed into plant transformation vectors pBI121 and pZP212. The resulted recombinant plasmids pZP212-ABP2, pZP212-ABP4 and pBI121-ABP9 were then respectively transformed into *Agrobacterium* and transgenic Arabidopsis plants were obtained by plant transformation using the resultant *Agrobacterium* recombinants. Survival analysis of the transgenic plants under different stress conditions shows that ABP2, ABP4 and ABP9 each can improve plant tolerance to abiotic stresses, for example, cold, salt and drought. The expression vectors and cell lines containing the inventive genes ABP2, ABP4, and ABP9, as well as the plant varieties harboring inventive genes with improved tolerance to abiotic stresses will also be in the scope of the invention.

The present invention successfully isolated and cloned from maize the genes ABP2, ABP4, and ABP9 encoding the transcription factors having ABRE binding specificity. This work will not only help to understand the ROS signal transduction pathway, but also provide strategies for generation of crop varieties with improved tolerance to stresses, such as drought, salinity and cold. The transcription factors expressed by the inventive genes can interact with the ABRE cis-element in the promoter region of multiple genes related to tolerance to abiotic stresses, and regulate the expression of the stress-related genes, and improve plant tolerance to abiotic stresses.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The patent or application file contains at least one drawing executed in color. Copies of this patent or patent application publication with color drawing(s) will be provided by the office upon request and payment of the necessary fee.

The present invention will become more fully understood from the detailed description and the accompanying drawings, wherein:

In FIG. 5. A stands for CK1, B for 1% NaCl, C for 0.8% NaCl, D for 0.6% NaCl, E for 150 mM $H_2O_2$, F for 60 mM $H_2O_2$, G for 10 mM $H_2O_2$, H for $H_2O$, I for 13% $H_2O$, J for 10% $H_2O$, K for 8% $H_2O$, L for $10^{-6}$M ABA, M for $10^{-5}$M ABA, N for $10^{-4}$M ABA, O for 4° C. and P for CK2.

DETAILED DESCRIPTION OF THE PREFERRED EMBODIMENTS

Example 1

Figure 1:
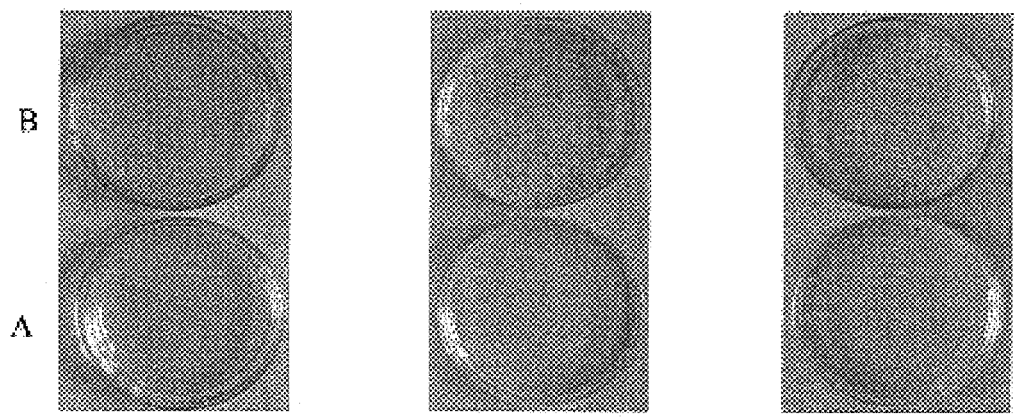
FIG. 1 shows the growth of yeast, showing the in vivo binding specificity of ABP2, ABP4 and ABP9 with ABRE.

Cloning and screening the genes encoding maize bZIP transcription factors.

Materials and Methods

1) Maize material: immature embryos of 17 days postpollination (17 dpp) from maize variety Qi 319.
2) Strains: E. coli DH5α, DH10B and JM109, and yeast strains yWAM2 (Leu$^-$, His$^-$, Trp$^-$).
3) Vectors: pBSK+, pRS315 and pPC86.
4) Restriction enzymes and modifying enzymes: restriction endonuclease and modifying enzyme are purchased from Promega Corp., New England Biolab, Inc. and Gibco Corporation.
5) Chemical reagents: the reagents for yeast culture are purchased from Sigma Chemical Company Ltd. and Oxford Corporation; the other chemical reagents are made in China (analytical pure).
6) Kits: Wizard™ Minipreps DNA Purification System and Wizard™ Maxipreps DNA Purification System available from Promega Corp. are used to extract plasmid DNA; DNA fragment quick purification/retrieve kit available from Ding Guo Biotechnology Ltd. is used to retrieve DNA; RNAgents Total RNA Isolation System kit and PolyATtract mRNA Isolation System available form Promega Corp. are used to extract RNA; and SuperScript™ Plasmid System for cDNA Synthesis and Plasmid Cloning kit available from GibcoBRL Company are used to construct the library.
7) Synthesis of primers: performed by Beijing Sai Bai Sheng Bioengineering Company and Shanghai Bioasia Biotechology Co., Ltd.
8) Sequencing: performed by Shanghai Bioasia Biotechology Co., Ltd.

Procedure of the Experiments

1) Total RNA Extraction and mRNA Isolation:

The total RNA extraction and the mRNA isolation are performed according to RNAgents Total RNA Isolation System kit and PolyATtract mRNA Isolation System available from Promega Corp., respectively. Weigh 1 g of maize 17dpp embryos, extract 2.834 mg of total RNA, and isolate 43.7 μg of mRNA.

2) Construction of cDNA Library With mRNA From Maize 17 dpp Embryos.

The construction is performed according to the protocol of SuperScript™ Plasmid System for cDNA Synthesis and Plasmid Cloning kit available from GibcoBRL Company. 5 μg of mRNA extracted from 17 dpp embryos was used to construct the cDNA library. The primer used in reverse transcription is:

Not I Adapter:

(SEQ ID NO: 8)
5'-pGACTAGTTCTAGATCGCGAGCGGCCGCCC(T)$_{15}$-3'.

Sal I Adapter was Added and Ligated to the Double-strand cDNA Synthesized:

5'-TCGACCCACGCGTCCG-3';         (SEQ ID NO: 16)

3'-GGGTGCGCAGGCp-5'.            (SEQ ID NO: 17)

Digest the ligation products with Not I and construct them into vector pPC86 (Trp$^+$). The vector was digested with Sal I and Not I, and purified. The construct was used to transform E. coli. DH10B and a cDNA library with the library capacity of 5.2×10$^6$ cfu was obtained.

3) Amplification of the cDNA Library:

Prepare 4 L of 2×LB culture medium (20 g/L Bactotryptone, 10 g/L Bacto-yease extract, 10 g/L NaCl, 3 g/L SeaPrep agarose, adjust to pH 7.0). Autoclave at 121° C. for 30 min. Incubate at 37° C. for 2 hours. Add penicillin G to a final concentration of 200 mg/L. To the medium, add the library up to a concentration of $10^6$ cfu/L. Mix well and aliquot 20-30 mL into 50-mL culture tubes. Ice-bath for 1 hour. Grow at 30° C. for 40 hours. Centrifuge at 8000 rpm for 10 min to collect the cells. Discard the supernatant. Add 200 mL of 2×LB (12.5% glycerol) to suspend the cells. Aliquot into 10mL/each container and store at −70° C. for later use.

4) Construction of Bait Vector Harboring 4mer ABRE and Specificity-testing Vector Containing 4mer Mutant ABRE (mABRE):

Synthesize the primers of ABRE(+)
5'GAAGTCCACGTGGAGGTGG3' (SEQ ID NO: 18) and ABRE(−)
5'TCCCACCTCCACGTGGACT3' (SEQ ID NO: 19). Remove 20 μl (1 μg/l) of ABRE(+) and ABRE(−) respectively, and mix well. Add 4 μl of 3M NaOAc and 100 μl of absolute ethanol. Place at −20° C. for 30 minutes. Centrifuge at 12000 rpm to pellet DNA. Wash once with 70% ethanol and dry. Add 6.5 μl of sterile $H_2O$ and 1 μl of 10×T4 polynucleotide kinase buffer. Then, anneal. The conditions for annealing are 88° C., 2 min; 65° C., 10 min; 37° C., 10 min; 25° C., 5 min. Add 1.5 μl of 20 mM ATP and 1 μl of T4 polynucleotide kinase. React at 37° C. for 2 hours. Extract with each of phenol-chloroform and chloroform once, respectively. Precipitate DNA with absolute ethanol. Then add 2 μl of 10× ligase buffer, 1 μl of ligase (5 units/μl) and 17 μl of sterile $H_2O$ to ligate overnight. Perform gel eletrophoresis with 2% agarose and isolate the DNA fragment of the size of about 80 bp. Clone the fragment into vector pBSK+ (digestion with Spe I and filling-in) and carry out sequencing. Obtain plasmid pA4.

Synthesize the primers: mABRE(+):
5'-GAAGTAACATGTTCGGTGG-3' (SEQ ID NO: 20);
mABRE(−): 5' TCCCACCGAACATGTTACT 3' (SEQ ID NO: 21). By the similar method as above, obtain plasmid pmA4.

Double-digest Vector pRS315His(Leu+) with BamH I and Xba I and purified. Similarly, digest plasmids pA4 and pmA4, and purified. Clone 4mer ABRE and 4mer InABRE into pRS315His, and obtain bait vector pRSA4(Leu+) and specificity-testing vector pRSmA4(Leu+), respectively.

5) Screening the 17 dpp cDNA Library:

Prepare yWAM2 competent cells. Transform pRSA4 into yeast strain yWAM2(Leu−, His−, Trp−) and obtain the yeast strain yA4 (His−, Trp−) containing pRSA4. The transformation may be performed according to Two Hybrid System TRAFO Protocol. Screen the library by the transformation of yA4 yeast with 17 dpp library DNA. Spread the transformed cells on His− selective medium and incubate at 28° C. for 3-5 days. When yeast colonies grow out, extract plasmid DNAs. The extraction method refers to Method I: Quick Plasmid DNA Preparations from Yeast (Christine Guthrie 1991). Transform E.Coli DH5α with the extracted plasmids and then extract plasmid DNAs from the resultant transformants. Analyse by enzyme-digestion. Perform sequencing and obtain the DNA sequences of the positive clones. Then analyse the sequences.

6) Acquirement of the Full-length cDNA Sequences of ABP2, ABP4 and ABP9:

The full-length cDNA sequences of ABP2, ABP4 and ABP9 are obtained by the method of 5'RACE. It is operated according to 5'RACE System for Rapid Amplification of cDNA Ends, Version 2.0 kit available from GibcoBRL Company.

The primers for reverse transcription:

ABP2 rv2: 5'-GCGACAGCGACGACAGATCA-3' (SEQ ID NO: 9)

ABP4 rv2: 5'-AGCGCCAGAAGCGGAGGCCA-3' (SEQ ID NO: 10)

ABP9 rv2: 5'-CCTTCACCAGGAAGTCCTCCA-3' (SEQ ID NO: 11)

The primers for PCR:

AUAP fw: 5'-GGCCACGCGTCGACTAGTAC-3' (SEQ ID NO: 12)

ABP2 rv3: 5'-AGGAACTCCTCCAGAGTCAT-3' (SEQ ID NO: 13)

ABP4 rv3: 5'-TCGTCGAACGTCAACGAGTAG-3' (SEQ ID NO: 14)

ABP9 rv3: 5'-AACCAATCCTCCGTTCTCACC-3' (SEQ ID NO: 15)

The conditions for PCR are 94° C. 3 min, 94° C. 30 sec, 60° C. 30 sec, 72° C. 1 min for 35 cycles, and then 72° C., 5 min. Isolate the amplified DNA fragments with 1% agarose gel and retrieve the target fragments. Ligate it into pGEM-T easy vector and transform E. coli. JM109. Identify clones by enzyme-digestion and then perform sequencing. Obtain the full-length cDNA sequences of the genes of ABP2, ABP4, and ABP9, respectively, which were named as sequences 1, 3 and 5 in the sequence listing. Based upon the cDNA sequences, the predicted proteins have the amino acid sequences set forth by sequences 2, 4 and 6 in the sequence listing.

Example 2

In vivo ABRE-Binding Specificity Analysis of ABP2, ABP4 and ABP9

Transform plasmids pRSA4(Leu+) and pRSmA4(Leu+) respectively into yWAM2 yeast and obtain yA4 and ymA4 yeast strains. Transform yA4 and ymA4 yeast with each of the ABP2, ABP4 and ABP9 plasmids obtained through screening the library. Incubate on His− selective medium for 3-5 days at 28° C. Only yA4 yeast transformed with ABP2, ABP4 or ABP9 plasmid can grow while ymA4 yeast transformed with ABP2, ABP4 or ABP9 plasmid cannot grow. The result means that ABP2, ABP4 or ABP9 is able to specifically bind to ABRE element in yeast and activate the expression of the reporter gene HIS3, thereby having the ability of growing in His− selective medium (FIG. 1B). In contrast, because ABP2, ABP4 or ABP9 cannot bind to mABRE and thereby cannot activate the expression of the reporter gene HIS3 that makes yeast not to grow on His selective medium (FIG. 1A). Therefore, ABP2, ABP4 and ABP9 have the in vivo ABRE-binding specificity in yeast cells.

Example 3

Analysis of in vitro ABRE-binding Specificity of ABP2, ABP4 and ABP9 (EMSA Test)

1) Purification of Proteins ABP2, ABP4 and ABP9:

Clone the full-length genes ABP2, ABP4 or ABP9 into prokaryote expression vector pGEX4T-1 and then transform into strain BL21. Induce the expression with 0.3 mM IPTG at 37° C. for 2-3 hours. SDS-PAGE eletrophoresis shows the specific expression bands of ABP2, ABP4 and ABP9. The purification of proteins ABP2, ABP4 and ABP9 is performed as MicroSpin™ GST Purification ModuLe protocol available from Pharmacia Corporation. The purified proteins are used for the EMSA test.

2) Isotope Labeling of ABRE and mABRE:

Use DNA 5' End-Labeling System of Promega Corp to label probes. The reaction system is: 1 µl of ABRE (or mABRE), 5 µl of $T_4$ PNK 10×buffer, 3 µl of $\gamma$-$^{32}$P-ATP, 2 µl of $T_4$ PNK (10U/µl), and 39 µl of $H_2O$. React at 37° C. for 20 minutes. Add 2 µl of 0.5M EDTA and stop the reaction at 68° C. for 10 minutes. Then keep at 37° C. for 10 minutes. Store at 4° C. for use.

Binding Reaction of Proteins ABP2, ABP4 and ABP9 with DNA:

Add 4 µl of 5×binding buffer (125 mM HEPES-KOH pH7.6, 50% glycerol, 250 mM KC1). Add 4 µg (9 µl) of each of the proteins ABP2, ABP4, ABP9 and GST. Add 1 µl of 1M DTT, 1 µl of probe of the above-labeled ABRE (or InABRE) and 4 µl of $H_2O$. Incubate on ice for 30 minutes. Add 3 µl of sample buffer (0.025% bromophenol blue in sterile $H_2O$) and perform polyacrylamide gel eletrophoresis analysis.

Figure 2:
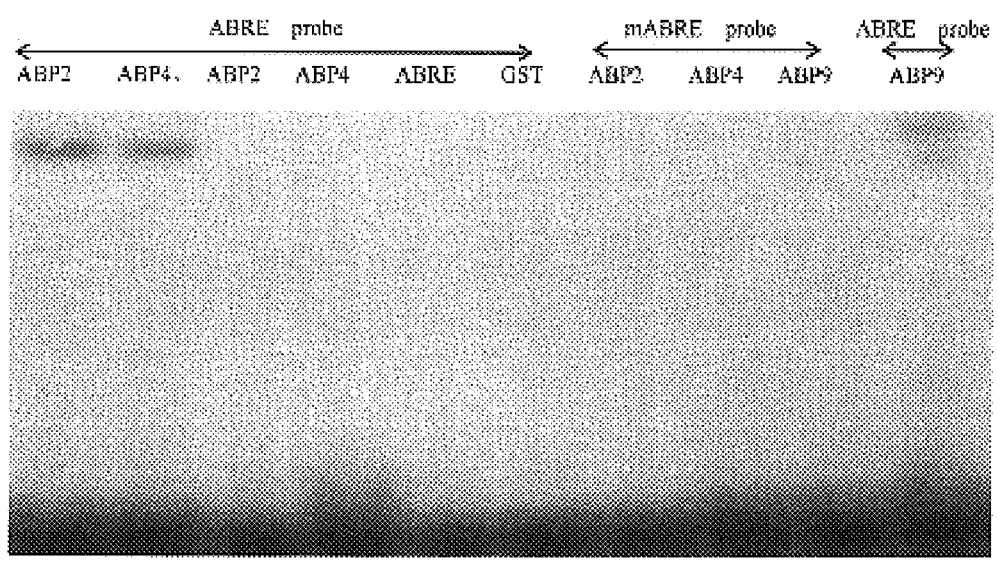
FIG. 2 illustrates the result of non-denature polyacrylamide gel electrophoresis, showing the in vitro binding specificity of ABP2, ABP4 and ABP9 to ABRE.

4) Non-denature Polyacrylamide Gel Eletrophoresis:

Preparation of Polyacrylamide Gel (5.4%):

Set up the gel mixture of 9 ml of 30% acrylamide, 5 ml of 10×eletrophoresis buffer (142.7 g/L glycin, 3.92 g/L EDTA, 30.28 g/L Tris), 2.5 ml of 50% glycerol, 33 ml of deionized water, 400 µl of 10% APS, and 25 µl of TEMED. After completion of polymerization, perfom gel eletrophoresis with 1×eletrophoresis buffer, including pre-running for 10 minutes (300V), loading the samples and eletrophoresis for 1 hour (300V). Stick the gel with filter paper to peel off. Seal the peeled gel with Saran wrap and expose to X ray film for 1 hour. Wash the film, develop for 2 minutes and fix for 5 minutes. The result shows that there exists a band of ABRE retarded significantly by proteins ABP2, ABP4 and ABP9 while there does not exist a band of mABRE retarded by them (FIG. 2). This means that the products of the genes ABP2, ABP4, and ABP9 also have the ABRE binding specificity in vitro.

Example 4

ABRE binding specificity and transcription activation function of ABP2, ABP4 and ABP9 in yeast and maize cells.

1) Transcription Activation Test in Yeast Cells

Figure 3:
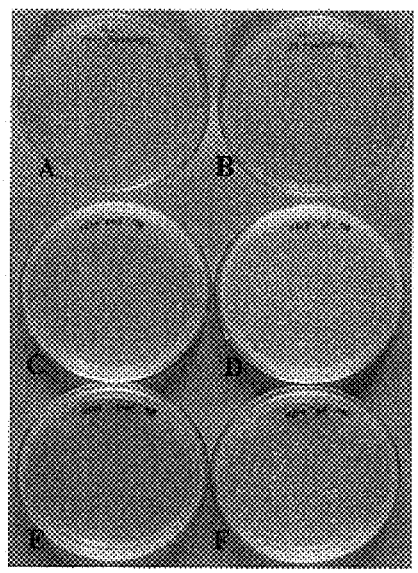
FIG. 3 illustrates the growth of yeast, showing the in vivo ABRE binding specificity and the transcriptional activation function of ABP2, ABP4 and ABP9 in yeast.

Construct the genes ABP2, ABP4 and ABP9 into yeast expression vector YepGAP(Trp$^+$) to obtain plasmids Yep-GAPABP-2, YepGAPABP-4 and YepGAPABP-9 containing the full-length cDNA of the genes ABP2, ABP4, and ABP9, respectively. Transform them into yA4 and ymA4 yeast and incubate the transformed yeast in His$^-$ selective medium at 28° C. for 3~5 days. The result shows that yA4 transformed by plasmid YepGAPABP-2, YepGAPABP-4, YepGA-PABP-9 can grow (FIG. 3B, D and F) while ymA4 transformed by them cannot grow (FIG. 3A, C and E). Therefore, ABP2, ABP4 and ABP9 not only have the ABRE binding specificity in yeast cells, but also have the transcription activation function. In FIG. 3, the capital letter A stands for ymA4+ABP2, B for yA4+ABP2, C for ymA4+ABP4, D for yA4+ABP4, E for ymA4+ABP9 and F for yA4+ABP9.

2) Test of Transcription Activation Function in Maize Cells

Construction of reporter plasmid: pIG46 vector is digested with Xho I and filled in with T4 DNA polymerase. Digest 4mer ABRE in vector pBluescript II SK+ with Sma I and Ecl136 II. Retrieve the DNA fragment of the size of about 80 bp used to ligate with the vector. Transform E. coli DH5α and extract the plasmid. Identify through enzyme digestion. The sequencing result shows that ABRE has been ligated upstream of 35S mini promoter.

Figure 4:
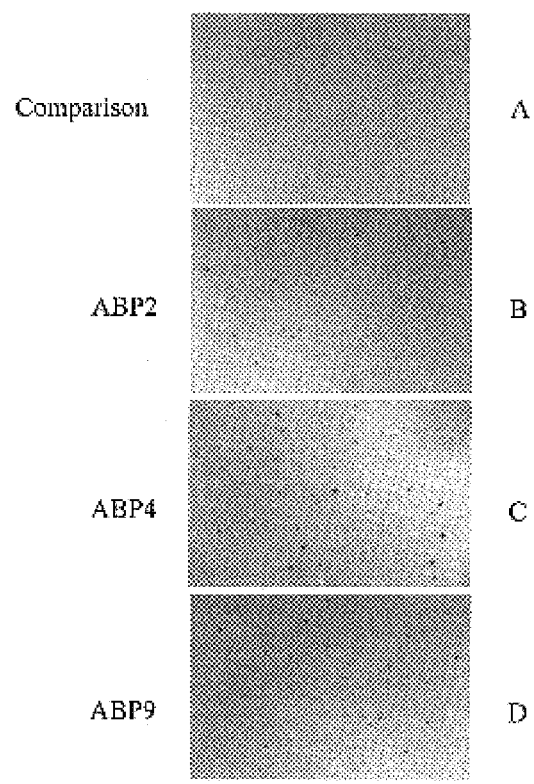
FIG. 4 shows the transformed maize suspension cells, showing the ABRE binding specificity and transcriptional activation function of ABP2, ABP4 and ABP9 in maize cells.

Construction of effector plasmids of ABP2, ABP4 and ABP9: The full-length cDNA of the genes ABP2, ABP4 and ABP9 (Xba I, Xho I) is constructed into plant expression vector pBI221 and obtain plasmids pBI221-ABP2, ABP4 and ABP9. Co-transform the reporter plasmid and effector plasmid into maize cells by bombardment. The materials for transformation are the maize suspension cells and the transformation method may refer to The Practical Methods of Molecular Biology and Biotechnology in Plant edited by B. R. Greenter and J. E. Tompson. The result shows that the reporter gene is not expressed when solely transformed with reportor plasmid (FIG. 4A) while it is significantly expressed when co-transformed with pIG46 and pBI221-ABP2, ABP4 or ABP9 (FIG. 4B, C and D). Therefore, the proteins ABP2, ABP4 and ABP9 not only have the ABRE binding specificity in maize cells, but also have the transcription activation function.

Example 5

Analysis of the expression specificity of ABP2, ABP4 and ABP9 under abiotic stresses 1) Treatment of maize materials: take maize seed and imbibe water for 24 hours. After planting in pot, grow at 28° C. with 12 hours photoperiod for about 20 days. Treat the plants at the development stage of three leaves with different conditions.

i. cold treatment: place the maize seedling in a 2° C. chamber and grow for 48 hours with 12 hours phtoperiod. Take out and wash off the soil on the root. Freeze with liquid nitrogen and store at −80° C. for use.

ii. salt treatment: place maize seedling in 0.6%, 0.8% and 1% NaCl solution, respectively. Grow with 12 hours photoperiod for 3 days. Take out and wash off the soil on the root. Freeze with liquid nitrogen and store at −80° C. for use:

iii. drought treatment: place maize seedling in the soil containing 8% (prepared by mixing 920 g of dry soil and 80 mL of water), 10% and 13% of water, respectively. Grow for 3 days, with 12 hours photoperiod. Take out and wash off the soil on the root. Freeze with liquid nitrogen and store at −80° C. for use.

iv. ABA treatment: place maize seedling in the solutions of $10^{-4}$M, $10^{-5}$M, $10^{-6}$M ABA respectively (weigh 5mg of ABA and dissolve in 0.1N KOH. Add into 95 mL of water up to a final concentration of $10^{-4}$M). Grow for 24 hours, with 12 hours photoperiod. Take out and wash off the soil on the root. freeze with liquid nitrogen and store at −80° C. for use.

v. $H_2O_2$ treatment: place maize seedling in the aqueous solutions of 10 mM $H_2O_2$ (1.13 ml of 30% $H_2O_2$/1), 60 mM $H_2O_2$ (6.78 ml of 30% $H_2O_2$/1), 150 mM $H_2O_2$ (14.95 ml of 30% $H_2O_2$/1). Grow for 24 hours, with 12 hours photoperiod. Take out and wash off the soil on the root. Deepfreeze with liquid nitrogen and store at −80° C. for use.

vi. water treatment: place maize seedling in water. Grow for 24 hours with 12 hours photoperiod. Freeze and store at −80° C.

vii. control: take the non-treated seedling and freeze at −80° C. as the control group.

2) Extract of RNA and Removal of DNA:

i. take about 200 mg of the treated maize materials and ground under the protection of liquid nitrogen. The method of RNA extract refers to RNAgents Total RNA Isolation System kit available from Promega Corp.

ii. dissolve RNA in 85 μl of water. Add 10 μl of 10×buffer and 5 μl of RQ1 RNase Free DNase (1U/μl). Incubate at 37° C. for 15 minutes to eliminate the DNA contamination.

iii. add 100 μl of phenol-chloroform to extract once. Remove the supernatant and precipitate RNA with equal volume of isopropanol. Wash once with 70% ethanol and dissolve in 50 μl of water.

iv. adjust the concentration of RNA to 1 μg/μl.

3) RT-PCR:

Add 1 μl of Oligo $dT_{18}$ (0.5 μg/μl), 5 μl of RNA (1 μg/μl), 1 μl of dNTP (10 mM) and 27 μl of $H_2O$. Treat at 65° C. for 5 minutes and at 0C for 2 minutes. Add 10 μl of 5×buffer, 5 μl of DTT (100 mM), and 10 U of RNase Inhibitor (40 U/μl). Treat at 42° C. for 2-5 minutes. Add 1 μl of SuperScipt II (200 u/μl). React at 42° C. for 50 minutes. Inactivate at 70° C. for 15 minutes for use.

The relative quantification of cDNA template and the design of interior label primers: Based upon the DNA sequence of maize actin gene (Maize Actin1 gene: Accession NO. J01238) in GenBank, design the following primers:

```
mAct1 F: 5'-CACCTTCTACAACGAGCTCCG-3'    (SEQ ID NO: 22)

mAct1 R: 5'-TAATCAAGG GCAACGTAGGCA-3'   (SEQ ID NO: 23)
```

Use the primers to perform the amplification. If it is amplified from cDNA, a 405 bp band will be amplified. And if it is amplified from genomic DNA, a 512 bp band will be amplified (containing a intron of 107 bp).

The reation mixture for PCR: 1 μl of template, 10 μl of 2×PCR buffer, 1 μl of 10 mM dNTP, 1 μl of 10 μM mAct1 F, 1 μl of 10 μM mAct1 R, 1U of Taq and 6 μl of sterile $H_2O$.

The conditions for PCR are 94° C. 2 min, 94° C. 30 sec, 55° C. 30 sec, 72° C. 30 sec for 30 cycles, and 72° C. 5 min.

Based upon the eletrophoresis result of PCR product, dilute the template DNA and adjust the amount of template DNA to be used. When the bands to be amplified by using mAct1 F and mAct1 R primers are substantially consistent, the amount of template cDNA in the samples is substantially consistent.

4) PCR amplication of the genes ABP2, ABP4, and ABP9:

i. ABP2: Design the primers for PCR amplification as follows (to amplify the fragment of 548 bp):

```
FW1 5'-TGATCTGTCGTCGCTGTCGC-3'    (SEQ ID NO: 24)

RV  5'-ACTCCAGGTTACTTGCATTAT-3'   (SEQ ID NO: 25)
```

The PCR system: 1 μl of template, 10 μl of 2×PCR buffer, 1 μl of 10 mM dNTP, 1 μl of 10 μM mAct1 F, 1 μl of 10 μM mAct1 R, 1U of Taq and 6 μl of sterile $H_2O$.

The PCR conditions are 94° C. 2 min, 94° C. 30 sec, 55° C. 30 sec, 72° C. 30 sec for 30 cycles, and 72° C. 5 min.

ii. ABP4: Design the primers for PCR amplification as follows (to amplify the fragment of 632 bp):

```
W1R 5'-TCGGTTATTCCCAATACACA-3'    (SEQ ID NO: 26)

W2F 5'-AGCAGCGGTGAACCAGCTTG-3'    (SEQ ID NO: 27)
```

The PCR system: 1 μl of template, 10 μl of 2×PCR buffer, 1 μl of 10 mM dNTP, 1 μl of 10 μM mAct1 F, 1 μl of 10 μM mAct1 R, 1U of Taq and 6 μl of sterile $H_2O$.

The conditions for PCR are 94° C. 2 min, 94° C. 30 sec, 55° C. 30 sec, 72° C. 30 sec for 30 cycles, and 72° C. 5 min.

iii. ABP9: Design the primers for PCR amplification as follows (to amplify the fragment of 937bp):

```
FW1 5'-CATGACGCTGGAGGACTTCCT-3'   (SEQ ID NO: 28)

RV  5'-TTGACGAAAACACAGAGC-3'      (SEQ ID NO: 29)
```

The PCR system: 1 μl of template, 10 μl of 2×PCR buffer, 1 μl of 10 mM dNTP, 1 μl of 10 μM mAct1 F, 1 μl of 10 μM mAct1 R, 1U of Taq and 6 μl of sterile $H_2O$.

Figure 5:
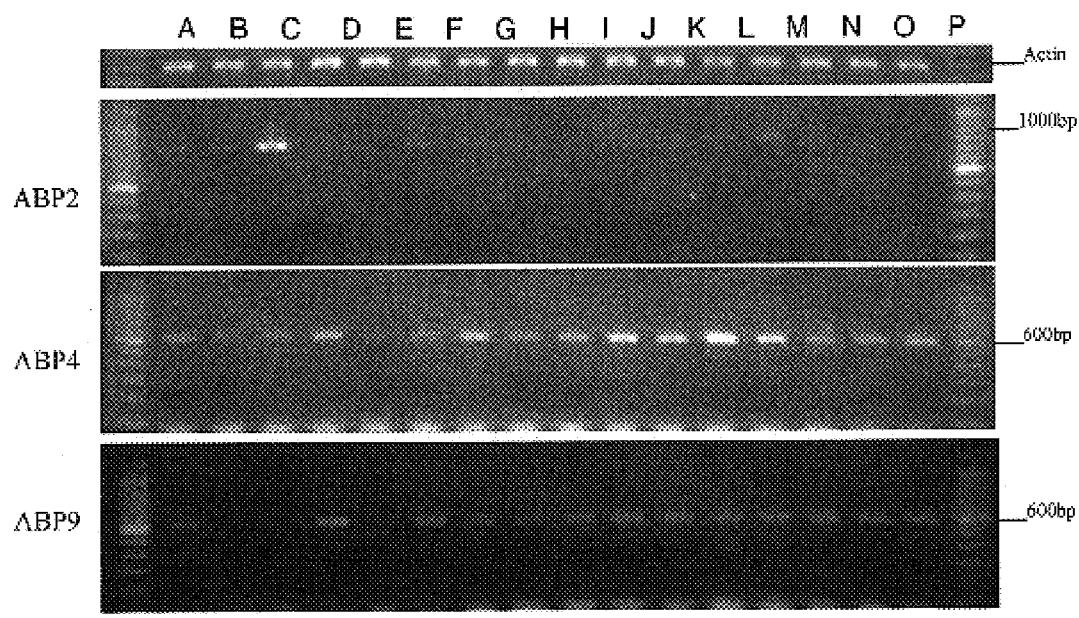
FIG. 5 demostrates the electrophoresis pattern of PCR, showing the induction of ABP2, ABP4 and ABP9 under stress conditions, i.e., salt, drought, hydrogen peroxide, ABA, low temperature. The conditions for PCR were 94° C. 2 min, 94° C. 30 sec, 55° C. 30 sec, 72° C. 50 sec for 30 cycles and 72° C. 5 min. The eletrophoresis result shows the expression of the genes ABP2, ABP4, and ABP9 can be induced by salt (FIG. 5A, B and C), drought (FIG. 5J and K), ABA (L, M and N), hydrogen peroxide (F and G).

The conditions for PCR are 94° C. 2 min, 94° C. 30 sec, 55° C. 30 sec, 72° C. 50 sec for 30 cycles and 72° C. 5 min. The eletrophoresis result shows the expression of the genes ABP2, ABP4, and ABP9 can be induced by salt (FIG. 5A, B and C), drought (FIG. 5J and K), ABA (L, M and N), hydrogen peroxide (F and G). In FIG. 5, A stands for CK1, B for 1% NaCl, C for 0.8% NaCl, D for 0.6% NaCl, E for 150 mM $H_2O_2$, F for 60 mM $H_2O_2$, G for 10 mM $H_2O_2$, H for $H_2O$, I for 13% $H_2O$, J for 10% $H_2O$, K for 8% $H_2O$, L for $10^{-6}$M ABA, M for $10^{-5}$M ABA, N for $10^{-4}$M ABA, O for 4° C. and P for CK2.

Example 6

Construction of transgenic expression vectors of ABP2, ABP4 and ABP9

1) Transformation of Arabidopsis with the Genes ABP2, ABP4 and ABP9:

The Cultivation of Arabidopsis

Vernalize arabidopsis seed at 4° C. for 2-3 day and plant 7-10 seeds in each pot (the rate of nutritive earth to vermiculite is 2:1). Grow in the greenhouse (at 22° C. with 16 hours light-treatment). After the arabidopsis grow out the primary bolting, snip off it. When the arabidopsis grow out many secondary boltings and a few of them begin to produce legumen, the plants can be used for transformation.

The Cultivation of *Agrobacterium*

Pick a single colony of *Agrobacterium* and inoculate into 3 ml of YEB (50 mg/L Kan and 50mg/l refampicin). Incubate at 28° C. with rotation at 250 rpm for 30 hours. 1:400 inoculate the seed culture into 200 ml of fresh YEB (50 mg/L Kan and 50mg/L refampicin) and incubate at 28° C. with rotation at 250 rpm for about 14 hours until $OD_{600}$ is about 1.5. Harvest the cells by centrifugation at 7500 rpm at 4° C. for 10 minutes. Re-suspend the cells in two volumes of liquid MS (400 ml) (1/2 MS salt +5% sucrose, pH5.7. Sterilized at 121° C. for 15 minutes). Immediately before use, add 6-BA to a final concentration of 0.044 μM, VB6 to a final concentration of 1 mg/l, VB1 to a final concentration of 10 mg/l, and SILWET to a final concentration of 0.02%).

i. Construction of plant expression vectors and transformation of *Agrobacterium*

Figure 6:
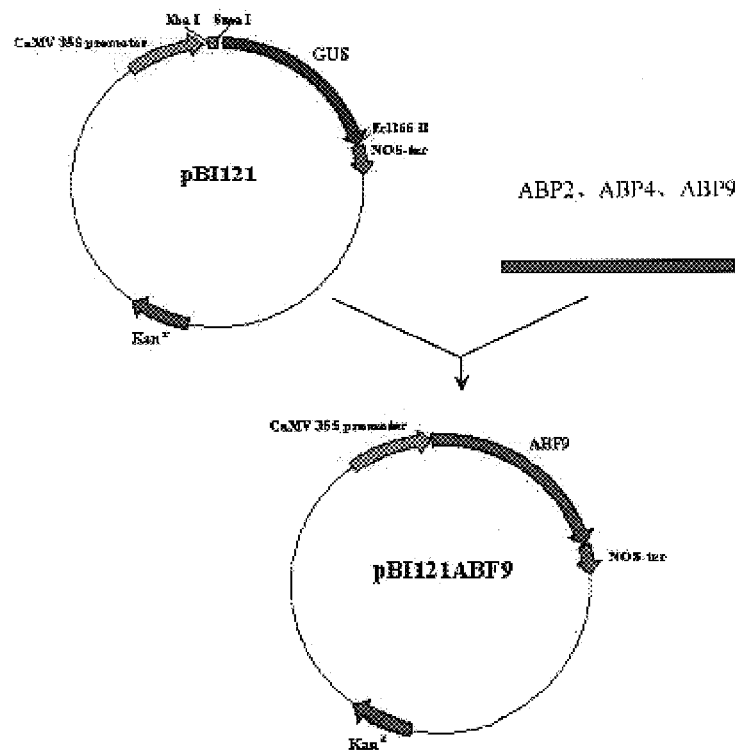
FIG. 6 is a construction diagram of plant expression vectors of ABP2, ABP4 or ABP9, showing the physical map of the expression vectors.

Construct genes ABP2, ABP4 and ABP9 into vectors pBI121 and pZP212 to obtain pZP212-ABP2, pZP212-ABP4 and pBI121-ABP9 (FIG. 6), respectively. Transform JM109, extract the plasmids and identify with digestion of enzymes. Pick out the desired clone, perform DNA sequencing and transform it into *Agrobacterium* LBA4404.

ii. Transformation of arabidopsis

Dip the bud of arabidopsis into *Agrobacterium* suspension under vacuum (25 IN Hg) for 5 minutes. After the transformation is over, cover the pot with a plastic bag. Place in horizontal direction. Let it grow under low light intensity for 24-48 hours. Then transfer to the normal conditions for further growth.

iii. Seed collection and screening

Weigh 25-30 mg of seeds collected from above transformation-treated plants and place into 1.5-mL centrifuge tube. Add 1 ml of 75% ethanol (containing 0.05% Tween 20) and shake in a shaker for 10 minutes (300 rpm). Centrifuge and discard the supernatant. Add 1 ml of 95% ethanol to wash one time, centrifuge and discard the supernatant. Repeat once. Add 0.3 ml of 100% ethanol and place on sterile filter paper under hood and blow-dry. Spread the blow-dried seeds on 1/2 MS plate (50 mg/l Kan) and place at 4° C. for 2 days. Grow at 22° C. and with 16 hours photoperiod. Transfer the antibiotics-resistant plants ($T_0$ generation) into pots for further cultivation and collect the seeds to perform the screening of $T_1$ generation.

2) Extraction of Genomic DNA from Antibiotics-resistant Arabidopsis Plants:

i. Ground 0.1-0.2 g of plant leaves under liquid nitrogen and transfer into 1.5-ml centrifuge tube.

ii. Add 0.7 ml of CTAB (100 mM Tris, 1.4 M NaCl, 20 mM EDTA, 2% CTAB, 0.1% mercaptoethanol) and place at 60° C. for 30 minutes. Note: turn over at an interval of 10 minutes.

iii. Add 0.7 ml of phenol: chloroform (1:1) and turn over for several times. Centrifuge at 10000 rpm for 5 minutes. Transfer the supernatant to a fresh centrifuge tube, add equal volume of chloroform: isopentanol (24:1), mix well, and centrifuge at 10000 rpm for 5 minutes. Transfer the supernatant to another fresh centrifuge tube.

iv. Add equal volume of isopropanol and turn over to mix well. Centrifuge at 10000 rpm for 10 minutes. Discard the supernatant. Wash once with 70% ethanol. Vacuum-dry. Dissolve in 50 µl of sterile $H_2O$ for PCR assay.

3) PCR Assay of Transgenic Arabidopsis:

```
forward primer:
                                               (SEQ ID NO: 30)
35S promoter: 5'-TCTGCCGACAGTGGTCCCAA-3' reverse primer:
                                               (SEQ ID NO: 13)
ABP2 rv3: 5'-AGG AAC TCC TCC AGA GTC AT-3'
```

```
                                               (SEQ ID NO: 14)
ABP4 rv3: 5'-TCG TCG AAC GTC AAC GAG TAG-3'

(SEQ ID NO: 15)
ABP9 rv3: 5'-AAC CAA TCC TCC GTT CTC ACC-3'
```

The reaction system (20 µl): 1 µl (20 ng~50 ng) of DNA from transgenic plant, 2 µl of 10×buffer, 2 µl of $MgCl_2$ (2.5 mM), 0.2 µl of Taq enzyme, 2 µl of dNTP (2.5 mM). Add 10 µM of each primer. Add sterile $H_2O$ up to the volume of 20 µl.

The reaction conditions are 94° C., 5 minutes; 94° C., 45 second; 60° C., 45 second; 72° C., 45 second for 35 cycles. Extend at 72° C. for 5 minutes. Identify the PCR positive plants.

Example 7

Survival analysis of transgenic plants of ABP2, ABP4 and ABP9 under stresses.

Figure 7:
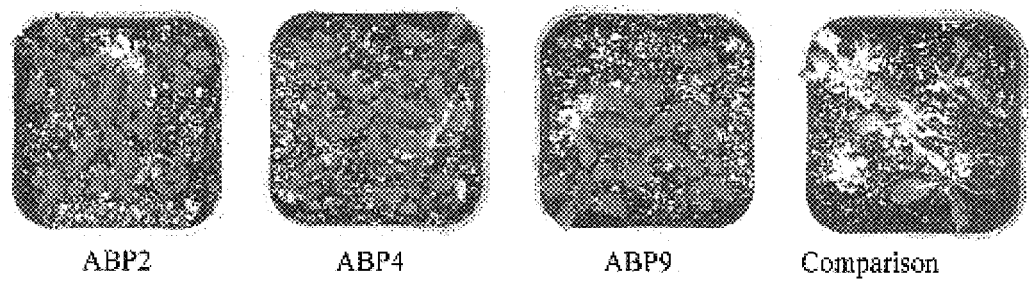
FIG. 7 shows the survival test of ABP2, ABP4 and ABP9 transgenic Arabidopsis under salt stress, as compared to non-transgenic Arabidopis ("comparison")

1) cold tolerance: place the transgenic plants and the non-trangenic plants at –6° C. for 6 hours. Then transfer into the normal growth conditions for recovery cultivation. The result shows that the survival rate of the transgenic plant is 80% while that of the non-transgenic plant is 10%. Therefore, ABP2, ABP4, and ABP9 are able to improve the cold tolerance of plants as shown in FIG. 7.

Figure 8:
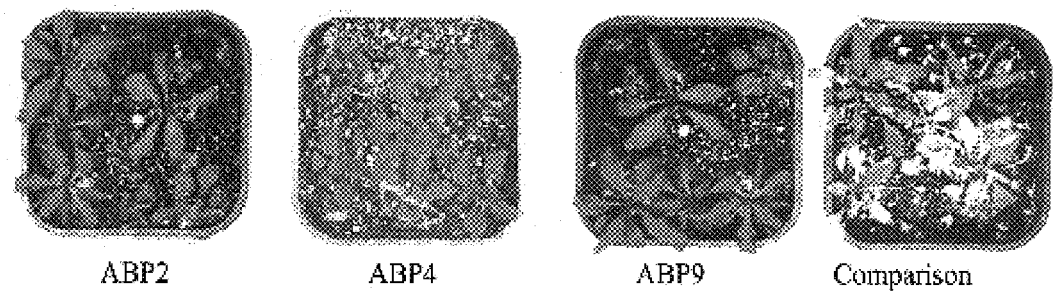
FIG. 8 shows the survival test of ABP2, ABP4 and ABP9 transgenic Arabidopsis under freezing temperature, as compared to non-transgenic Arabidopsis ("comparison")

2) salt tolerance: place the transgenic plants and the non-transgenic plants in 600 mM NaCl solution and immerse for 3 hours. Grow at 22° C. for 24 hours, under light. Transfer into the normal growth conditions for arabidopsis for recovery cultivation. The result shows that the survival rate of the transgenic plant is 80% while that of the non-transgenic plant is 15%. Therefore, ABP2, ABP4, and ABP9 are able to improve the salt tolerance of plants as shown in FIG. 8.

Figure 9:
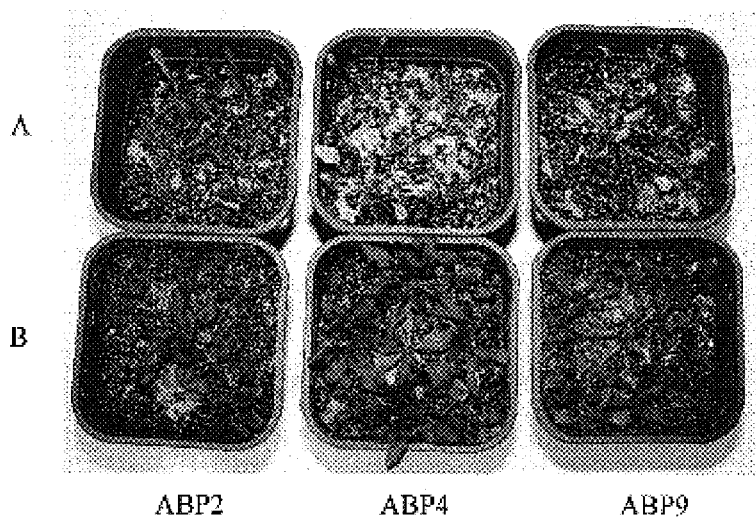
FIG. 9 shows the survival test of ABP2, ABP4 and ABP9 transgenic Arabidopsis under drought stress.

3) drought tolerance: place the transgenic plants and the non-transgenic plants under the normal growth conditions for arabidopsis. Continuously cultivate for 15-20 days without supplying water. The result shows that the survival rate of the transgenic plant is 90% while that of the non-transgenic plant is 5%. Therefore, ABP2, ABP4 and ABP9 are able to significantly improve the drought tolerance of plants as shown in FIG. 9, wherein the capital letter A stands for transgenic plant, B for non-transgenic plant.

APPLICATION IN INDUSTRY AND AGRICULTURE

The invention has successfully cloned the genes encoding maize bZIP transcription factors ABP2, ABP4, and ABP9, respectively. Furthermore, the invention has successfully introduced the genes into arabidopsis and obtains novel arabidopsis with enhanced tolerance to abiotic stresses. The work will have important theoretic and practical significance to breed new plant varieties with improved tolerance to abiotic stresses.

What is claimed is:

1. An isolated nucleic acid comprising the nucleotide sequence of SEQ ID NO: 5 or a nucleotide sequence encoding a protein which comprises the amino acid sequence of SEQ ID NO: 6, wherein SEQ ID NO: 6 represents maize bZIP transcriptional factor.

2. An expression vector comprising the isolated nucleic acid according to claim 1.

3. The expression vector according to claim 2 wherein said expression vector is pBI121-ABP9.

4. A cell line transformed with the isolated nucleic acid according to claim 1.

5. A plant material transformed with a DNA comprising a nucleotide sequence encoding a transcription regulating protein which comprises the amino acid sequence of SEQ ID NO: 6.

6. A chimeric plant expression vector, said vector comprising in the 5' to 3' direction: a heterologous promoter that is capable of effecting mRNA transcription in a selected plant cell to be transformed, operably linked to a structural DNA sequence encoding SEQ ID NO: 6 that induces abiotic stress tolerance and operably linked to a non-translated region of a gene, said region comprises a signal sequence for polyadenylation of mRNA.

7. A vector capable of introducing at least one regulatory gene encoding a protein into a plant, the vector comprising: (a) the nucleotide sequence of SEQ ID NO: 5 or (b) a nucleotide sequence encoding a protein comprising the amino acid sequence of SEQ ID NO: 6 and a promoter operably linked to the nucleotide sequence of (a) or (b).

8. The vector according to claim 7, further comprising a transcription terminator sequence operably linked to the nucleotide sequence of (a) or (b).

9. The vector according to claim 7, further comprising a nucleotide sequence encodinq a selective marker.

10. An *Agrobacterium tumefaciens* transformed with the vector according to claim 7.

* * * * *

SEQUENCE LISTING

```
<160> NUMBER OF SEQ ID NOS: 30

<210> SEQ ID NO 1
<211> LENGTH: 1485
<212> TYPE: DNA
<213> ORGANISM: Zea mays
```

```
<220> FEATURE:
<221> NAME/KEY: CDS
<222> LOCATION: (114)..(1166)

<400> SEQUENCE: 1
atccgccctc tggtttttca gagcagcagt ccaggcgcgg aattgaattc cggtaggatt      60
tgagagcgga gcggagcgga gaggagaggg gaagaaggcg gtaggcgggg aag atg        116
                                                              Met
                                                               1 gag atg ccg gca ggg agc ggg gcc cca gcg ctg gcg cgg cag ggc tcg       164
Glu Met Pro Ala Gly Ser Gly Ala Pro Ala Leu Ala Arg Gln Gly Ser
             5                  10                  15 gtc tac tcg ctc acg ttc gac gag ttc cag acc acg ctc ggc ggc gcc       212
Val Tyr Ser Leu Thr Phe Asp Glu Phe Gln Thr Thr Leu Gly Gly Ala
         20                  25                  30 agc aag gac ttc ggc tcc atg aac atg gac gag ctg ctg cgc aac atc       260
Ser Lys Asp Phe Gly Ser Met Asn Met Asp Glu Leu Leu Arg Asn Ile
     35                  40                  45 tgg aca gcc gag gag tct aac gcc atg gct gcg gcc gcc ccg gcc acg       308
Trp Thr Ala Glu Glu Ser Asn Ala Met Ala Ala Ala Ala Pro Ala Thr
 50                  55                  60                  65 gcc acg gcc acg gcg gcc gca tcc gtg gac gcg cac gcg cag cag cag       356
Ala Thr Ala Thr Ala Ala Ala Ser Val Asp Ala His Ala Gln Gln Gln
                 70                  75                  80 cag cag cag cag cac ggg gcg ccc atc cag cgc cag ggc tcc ttc acg       404
Gln Gln Gln Gln His Gly Ala Pro Ile Gln Arg Gln Gly Ser Phe Thr
             85                  90                  95 ctg ccc cgc aca ctc agc cag aag acg gtc gac gag gtc tgg cgc gag       452
Leu Pro Arg Thr Leu Ser Gln Lys Thr Val Asp Glu Val Trp Arg Glu
        100                 105                 110 atc gtg agc ctc acc agc ggc gag gac gcg cag cag gtt gcg gct ccc       500
Ile Val Ser Leu Thr Ser Gly Glu Asp Ala Gln Gln Val Ala Ala Pro
    115                 120                 125 gct ccc gct ccc gcg ccc gag ccc gag ccc gcg ccc gcg ccc gcg ccg       548
Ala Pro Ala Pro Ala Pro Glu Pro Glu Pro Ala Pro Ala Pro Ala Pro
130                 135                 140                 145 ctg ccg gcg cag gcg cag gcg cag cag acg ctg ggg tcc atg act ctg       596
Leu Pro Ala Gln Ala Gln Ala Gln Gln Thr Leu Gly Ser Met Thr Leu
                150                 155                 160 gag gag ttc ctg gta cgc gcc ggc gtg gtt cgt gag gac atg ggg ggg       644
Glu Glu Phe Leu Val Arg Ala Gly Val Val Arg Glu Asp Met Gly Gly
            165                 170                 175 cac cag acc ctc ctg ctg cag ccg cac gcg cag ggg ctt ttc tcc cag       692
His Gln Thr Leu Leu Leu Gln Pro His Ala Gln Gly Leu Phe Ser Gln
        180                 185                 190 ggg aat gcg gtc gcg ccg cag acc ctg cag ctg gga aac ggg atg gtg       740
Gly Asn Ala Val Ala Pro Gln Thr Leu Gln Leu Gly Asn Gly Met Val
    195                 200                 205 gcc ggg gtc gtc ggg cag ggc ctc gga gga ggg gtg acg gtg gcg gct       788
Ala Gly Val Val Gly Gln Gly Leu Gly Gly Gly Val Thr Val Ala Ala
210                 215                 220                 225 ccg acg acg ccg gtc gtg ttc aac ggg ttg gga aag gtg gag gcg ggt       836
Pro Thr Thr Pro Val Val Phe Asn Gly Leu Gly Lys Val Glu Ala Gly
                230                 235                 240 gat ctg tcg tcg ctg tcg ccg gtg ccg tat ccg ttc gac act gcg ctg       884
Asp Leu Ser Ser Leu Ser Pro Val Pro Tyr Pro Phe Asp Thr Ala Leu
            245                 250                 255 agg atg cgg aag gga ccc acc gtc gag aag gtg gtg gag agg agg cag       932
Arg Met Arg Lys Gly Pro Thr Val Glu Lys Val Val Glu Arg Arg Gln
        260                 265                 270
```

```
cgc cgc atg atc aag aac agg gag tcg gcc gcc agg tcg cgt gcg agg      980
Arg Arg Met Ile Lys Asn Arg Glu Ser Ala Ala Arg Ser Arg Ala Arg
275                 280                 285 aag cag gcg tac ata atg gag ctg gaa gct gag gtg gca aaa ctc aag     1028
Lys Gln Ala Tyr Ile Met Glu Leu Glu Ala Glu Val Ala Lys Leu Lys
290                 295                 300                 305 gac cag aat gag gag ttg cag aaa aag cag gtt gaa atg cta aag aag     1076
Asp Gln Asn Glu Glu Leu Gln Lys Lys Gln Val Glu Met Leu Lys Lys
            310                 315                 320 caa aag gat gag gtc ctg gag cga atc aac agc caa cat gga cca aag     1124
Gln Lys Asp Glu Val Leu Glu Arg Ile Asn Ser Gln His Gly Pro Lys
        325                 330                 335 gca aag aag ctt tgc ctg cgc cgc acc ctg act ggc cca tgg              1166
Ala Lys Lys Leu Cys Leu Arg Arg Thr Leu Thr Gly Pro Trp
    340                 345                 350 tagcctgctg aagcttgcac aaaattgacc gaagtcaaga tcgtcgggcc agatgtgccc    1226
gtgtgtatat atcagatgaa gtcaagagta ctgagtaccc cgttacccct gtagaccgcc    1286
gctacttcag agctgccgtt cttgttctgt gacgtgggta gtctgcgcct gacagttcgc    1346
tgtttaggtt cggttgcgcg atcctcacat gaacaatgag gcgtgccatc taatttgttt    1406
attaactcac tcctatctat ggtgagataa tgcaagtaac ctggagtaaa aaaaaaaaa    1466 aaaaaaaaaa aaaaaaaa                                                 1485

<210> SEQ ID NO 2
<211> LENGTH: 351
<212> TYPE: PRT
<213> ORGANISM: Zea mays

<400> SEQUENCE: 2

Met Glu Met Pro Ala Gly Ser Gly Ala Pro Ala Leu Ala Arg Gln Gly
1               5                   10                  15

Ser Val Tyr Ser Leu Thr Phe Asp Glu Phe Gln Thr Thr Leu Gly Gly
            20                  25                  30

Ala Ser Lys Asp Phe Gly Ser Met Asn Met Asp Glu Leu Leu Arg Asn
        35                  40                  45

Ile Trp Thr Ala Glu Glu Ser Asn Ala Met Ala Ala Ala Pro Ala
    50                  55                  60

Thr Ala Thr Ala Thr Ala Ala Ser Val Asp Ala His Ala Gln Gln
65                  70                  75                  80

Gln Gln Gln Gln Gln His Gly Ala Pro Ile Gln Arg Gln Gly Ser Phe
                85                  90                  95

Thr Leu Pro Arg Thr Leu Ser Gln Lys Thr Val Asp Glu Val Trp Arg
            100                 105                 110

Glu Ile Val Ser Leu Thr Ser Gly Glu Asp Ala Gln Gln Val Ala Ala
        115                 120                 125

Pro Ala Pro Ala Pro Glu Pro Glu Pro Ala Pro Ala Pro Ala
    130                 135                 140

Pro Leu Pro Ala Gln Ala Gln Ala Gln Thr Leu Gly Ser Met Thr
145                 150                 155                 160

Leu Glu Glu Phe Leu Val Arg Ala Gly Val Val Arg Glu Asp Met Gly
                165                 170                 175

Gly His Gln Thr Leu Leu Leu Gln Pro His Ala Gln Gly Leu Phe Ser
            180                 185                 190

Gln Gly Asn Ala Val Ala Pro Gln Thr Leu Gln Leu Gly Asn Gly Met
        195                 200                 205
```

```
Val Ala Gly Val Val Gly Gln Gly Leu Gly Gly Val Thr Val Ala
    210                 215                 220
Ala Pro Thr Thr Pro Val Val Phe Asn Gly Leu Gly Lys Val Glu Ala
225                 230                 235                 240
Gly Asp Leu Ser Ser Leu Ser Pro Val Pro Tyr Pro Phe Asp Thr Ala
                245                 250                 255
Leu Arg Met Arg Lys Gly Pro Thr Val Glu Lys Val Val Glu Arg Arg
                260                 265                 270
Gln Arg Arg Met Ile Lys Asn Arg Glu Ser Ala Ala Arg Ser Arg Ala
            275                 280                 285
Arg Lys Gln Ala Tyr Ile Met Glu Leu Glu Ala Glu Val Ala Lys Leu
        290                 295                 300
Lys Asp Gln Asn Glu Glu Leu Gln Lys Lys Gln Val Glu Met Leu Lys
305                 310                 315                 320
Lys Gln Lys Asp Glu Val Leu Glu Arg Ile Asn Ser Gln His Gly Pro
                325                 330                 335
Lys Ala Lys Lys Leu Cys Leu Arg Arg Thr Leu Thr Gly Pro Trp
            340                 345                 350

<210> SEQ ID NO 3
<211> LENGTH: 1834
<212> TYPE: DNA
<213> ORGANISM: Zea mays
<220> FEATURE:
<221> NAME/KEY: CDS
<222> LOCATION: (93)..(1172)

<400> SEQUENCE: 3
gtcttgaggc tttgagctct cctcacctcg tatccgtgtc tttctggtgc tgagctgagt      60
ctgagagaca ggtaaggagg aggagggtgg ag atg gaa ttc aag aac tgc ggg       113
                                   Met Glu Phe Lys Asn Cys Gly
                                    1               5 tcg tcg tcg cag ccc cgg ccg gcg gtg gta gtg ggc gag gag gcg gcg       161
Ser Ser Ser Gln Pro Arg Pro Ala Val Val Val Gly Glu Glu Ala Ala
         10                  15                  20 ttg gcg aga cag gga tca gtc tac tcg ttg acg ttc gac gaa ttc cag       209
Leu Ala Arg Gln Gly Ser Val Tyr Ser Leu Thr Phe Asp Glu Phe Gln
 25                  30                  35 agc gcg ctc ggc ggg gcc gcc acc ggc ggt ggc ggt ggc ggc agc atc       257
Ser Ala Leu Gly Gly Ala Ala Thr Gly Gly Gly Gly Gly Gly Ser Ile
40                  45                  50                  55 ccc aag gat ttc ggt tcc atg aac atg gac gaa ctg ctc cgg agc atc       305
Pro Lys Asp Phe Gly Ser Met Asn Met Asp Glu Leu Leu Arg Ser Ile
                 60                  65                  70 tgg acc gcg gag gag acc cag gcc atg gcc tcc gct tct ggc gct gga       353
Trp Thr Ala Glu Glu Thr Gln Ala Met Ala Ser Ala Ser Gly Ala Gly
             75                  80                  85 gcg ggt gcg ggg atg ccg cca acg tcg ctg cag cgg caa ggg tcg tcg       401
Ala Gly Ala Gly Met Pro Pro Thr Ser Leu Gln Arg Gln Gly Ser Ser
         90                  95                 100 ctc aca ctg ccc cgc acg ctc agc acc aag acg gtc gac gag gtg tgg       449
Leu Thr Leu Pro Arg Thr Leu Ser Thr Lys Thr Val Asp Glu Val Trp
105                 110                 115 cgc aat ctc gtg cgc gac gag ccg ctg cag ggg gcg gac ggc ggc ggg       497
Arg Asn Leu Val Arg Asp Glu Pro Leu Gln Gly Ala Asp Gly Gly Gly
120                 125                 130                 135 cac cag cag cac cac cgc cag tcg acg ctc ggg gag atg act ctg gag       545
His Gln Gln His His Arg Gln Ser Thr Leu Gly Glu Met Thr Leu Glu
```

```
                    140               145                150
gag ttc ttg gtc aga gct ggc gtg gtc agg gag aac ccc gct ccg gct        593
Glu Phe Leu Val Arg Ala Gly Val Val Arg Glu Asn Pro Ala Pro Ala
            155                 160                 165 cct cca gca cca cca ccc atg atc ccg ccg cgg ccg gta cct gtc gcc        641
Pro Pro Ala Pro Pro Pro Met Ile Pro Pro Arg Pro Val Pro Val Ala
            170                 175                 180 cct aaa agc tcc gcc ttt ttc ggg aat tta ccg ggt gcc gac gcc gac        689
Pro Lys Ser Ser Ala Phe Phe Gly Asn Leu Pro Gly Ala Asp Ala Asp
        185                 190                 195 acc gcc gca gct gcg gca gcg ctg ggg ttt gca ccg gtc ggc atg ggg        737
Thr Ala Ala Ala Ala Ala Leu Gly Phe Ala Pro Val Gly Met Gly
200                 205                 210                 215 gat ctg gcc caa ata ccg ccc agg gca gca ggc atg gga ggc ggc gcc        785
Asp Leu Ala Gln Ile Pro Pro Arg Ala Ala Gly Met Gly Gly Gly Ala
                220                 225                 230 atg gct gtg caa gca gcg gtg aac cag ctt gat tct ggc ggg aag ggg        833
Met Ala Val Gln Ala Ala Val Asn Gln Leu Asp Ser Gly Gly Lys Gly
            235                 240                 245 tac agc gac ctg tcg tcg ccg acg gag ccg ctc ccg ttt tcg ttt gag        881
Tyr Ser Asp Leu Ser Ser Pro Thr Glu Pro Leu Pro Phe Ser Phe Glu
        250                 255                 260 ggg atg att cga ggg agg agg cat ggg ggc gga gta gag aaa gtg gtg        929
Gly Met Ile Arg Gly Arg Arg His Gly Gly Gly Val Glu Lys Val Val
265                 270                 275 gag agg cgg cag agg agg atg atc aag aac agg gag tcc gcc gcc agg        977
Glu Arg Arg Gln Arg Arg Met Ile Lys Asn Arg Glu Ser Ala Ala Arg
280                 285                 290                 295 tcc cga gcg cgc aaa cag gct tat act atg gag tta gaa gct gaa gtt       1025
Ser Arg Ala Arg Lys Gln Ala Tyr Thr Met Glu Leu Glu Ala Glu Val
                300                 305                 310 cag aaa ctc aag gag cag aat cag gaa ctg gag agg aaa cag gca gag       1073
Gln Lys Leu Lys Glu Gln Asn Gln Glu Leu Glu Arg Lys Gln Ala Glu
            315                 320                 325 att atg gaa atg cag aag aac gag cta cca gaa atg ttg aag gat cca       1121
Ile Met Glu Met Gln Lys Asn Glu Leu Pro Glu Met Leu Lys Asp Pro
        330                 335                 340 ttc gga cgg aag aag cgt ctg tgc ttg cga aga aca ttg act ggg cct       1169
Phe Gly Arg Lys Lys Arg Leu Cys Leu Arg Arg Thr Leu Thr Gly Pro
    345                 350                 355 tgg tgatgactat ctgaaacagc agacgagtcg cgctgcatac ctgcagtggt            1222
Trp
360 gcttgggatc tgtacacaat ttgtctccta tagactagcg atggacgtag tggggatgat    1282 tgtactgtta ccgcttaggg cttgttcggt tagctctcaa tccatgtgga ttgagcggga    1342 ttggatgggt ttgaatccca acaagtcaa acttcttcac aatttttcc aatcccatcc      1402 aatccatgtg tattgggaat aaccgaacaa gcccttatag tggagtcgga aactgacaca    1462 tgtagattat gttagtagag aaccaaatgg agtgaagccg ccgcgcaag actcgggctt     1522 cagccatcct ccagagcttg tgtagagttg cctagctttg catcttgcca gagccagcac    1582 gtcgtgtaga gattggacgg ttttaaaaga tcggtggctg ggtgtaagta ggttggtggg    1642 attacaagca tgggcatggc gacgttcagg atgcaaccgg cttgacgact gtacgtacat    1702 ctgatggctg tagagctgta gtatgcaaac tgtcccgctg ctgcttgtgt gtaatggtga    1762 aaccagatga atcggttatt tgtgtattac ttagcaaata tgctcacaag gatttcaaaa    1822 aaaaaaaaaa aa                                                        1834
```

<210> SEQ ID NO 4
<211> LENGTH: 360
<212> TYPE: PRT
<213> ORGANISM: Zea mays

<400> SEQUENCE: 4

Met Glu Phe Lys Asn Cys Gly Ser Ser Gln Pro Arg Pro Ala Val
1               5                   10                  15

Val Val Gly Glu Glu Ala Ala Leu Ala Arg Gln Gly Ser Val Tyr Ser
            20                  25                  30

Leu Thr Phe Asp Glu Phe Gln Ser Ala Leu Gly Gly Ala Thr Gly
            35                  40                  45

Gly Gly Gly Gly Ser Ile Pro Lys Asp Phe Gly Ser Met Asn Met
50                  55                  60

Asp Glu Leu Leu Arg Ser Ile Trp Thr Ala Glu Glu Thr Gln Ala Met
65                  70                  75                  80

Ala Ser Ala Ser Gly Ala Gly Ala Gly Met Pro Pro Thr Ser
            85                  90                  95

Leu Gln Arg Gln Gly Ser Ser Leu Thr Leu Pro Arg Thr Leu Ser Thr
            100                 105                 110

Lys Thr Val Asp Glu Val Trp Arg Asn Leu Val Arg Asp Glu Pro Leu
            115                 120                 125

Gln Gly Ala Asp Gly Gly His Gln Gln His Arg Gln Ser Thr
130                 135                 140

Leu Gly Glu Met Thr Leu Glu Glu Phe Leu Val Arg Ala Gly Val Val
145                 150                 155                 160

Arg Glu Asn Pro Ala Pro Ala Pro Ala Pro Pro Met Ile Pro
            165                 170                 175

Pro Arg Pro Val Pro Val Ala Pro Lys Ser Ser Ala Phe Phe Gly Asn
            180                 185                 190

Leu Pro Gly Ala Asp Ala Asp Thr Ala Ala Ala Ala Ala Leu Gly
            195                 200                 205

Phe Ala Pro Val Gly Met Gly Asp Leu Ala Gln Ile Pro Pro Arg Ala
210                 215                 220

Ala Gly Met Gly Gly Gly Ala Met Ala Val Gln Ala Ala Val Asn Gln
225                 230                 235                 240

Leu Asp Ser Gly Gly Lys Gly Tyr Ser Asp Leu Ser Ser Pro Thr Glu
            245                 250                 255

Pro Leu Pro Phe Ser Phe Glu Gly Met Ile Arg Gly Arg His Gly
            260                 265                 270

Gly Gly Val Glu Lys Val Val Glu Arg Arg Gln Arg Met Ile Lys
            275                 280                 285

Asn Arg Glu Ser Ala Ala Arg Ser Arg Ala Arg Lys Gln Ala Tyr Thr
290                 295                 300

Met Glu Leu Glu Ala Glu Val Gln Lys Leu Lys Glu Gln Asn Gln Glu
305                 310                 315                 320

Leu Glu Arg Lys Gln Ala Glu Ile Met Glu Met Gln Lys Asn Glu Leu
            325                 330                 335

Pro Glu Met Leu Lys Asp Pro Phe Gly Arg Lys Arg Leu Cys Leu
            340                 345                 350

Arg Arg Thr Leu Thr Gly Pro Trp
            355                 360

```
<210> SEQ ID NO 5
<211> LENGTH: 1510
<212> TYPE: DNA
<213> ORGANISM: Zea mays
<220> FEATURE:
<221> NAME/KEY: CDS
<222> LOCATION: (45)..(1199)

<400> SEQUENCE: 5
taaaaggagt ctttgcagtt gcaggtcgag tgtctagata tgat atg gcg tcg gag        56
                                                Met Ala Ser Glu
                                                 1 acg acc aag aac gtg aag gcc acc ctc gac gag cag gag gta acc tcg       104
Thr Thr Lys Asn Val Lys Ala Thr Leu Asp Glu Gln Glu Val Thr Ser
  5              10                  15                  20 cat cag cgc gac cag agc gct gcc gag gag gag gag gtg gtg gta gtg       152
His Gln Arg Asp Gln Ser Ala Ala Glu Glu Glu Glu Val Val Val Val
             25                  30                  35 gtg gat ccg ctg gcg cgg cag tcg tcc gtc atg tcg ctt acg ctg gag       200
Val Asp Pro Leu Ala Arg Gln Ser Ser Val Met Ser Leu Thr Leu Glu
         40                  45                  50 gag ctg cag agc tcg ctc tgc gag ccg ggg cgc aac ttc ggg tcc atg       248
Glu Leu Gln Ser Ser Leu Cys Glu Pro Gly Arg Asn Phe Gly Ser Met
     55                  60                  65 aac atg gac gag ttc atg gcc aac ata tgg aac gcc gag gag ttc cag       296
Asn Met Asp Glu Phe Met Ala Asn Ile Trp Asn Ala Glu Glu Phe Gln
 70                  75                  80 gcc gcc acc gcc acc gcc acc ggc ggc tgc agc aag cag gag ggc acg       344
Ala Ala Thr Ala Thr Ala Thr Gly Gly Cys Ser Lys Gln Glu Gly Thr
 85                  90                  95                 100 cag cgg gag ccg atg atg ccc gtg gcg aat gga aca ggt gag aac gga       392
Gln Arg Glu Pro Met Met Pro Val Ala Asn Gly Thr Gly Glu Asn Gly
                105                 110                 115 gga ttg gtt cgg cag gcc aac gcg gcg gcg cag gcc gtg gtg cag ccc       440
Gly Leu Val Arg Gln Ala Asn Ala Ala Ala Gln Ala Val Val Gln Pro
            120                 125                 130 cag atg ggg agc ggc ggt ggc ggc ggc gtc gcc gcc agc ggg cgg       488
Gln Met Gly Ser Gly Gly Gly Gly Gly Val Ala Ala Ser Gly Arg
        135                 140                 145 cag cag gtg acg ctg gcc gac atg acg ctg gag gac ttc ctg gtg aag       536
Gln Gln Val Thr Leu Ala Asp Met Thr Leu Glu Asp Phe Leu Val Lys
    150                 155                 160 gct ggc gtc gtg cga gga gcc ttc gcc ggc cac ggc cac gcg gtc gtc       584
Ala Gly Val Val Arg Gly Ala Phe Ala Gly His Gly His Ala Val Val
165                 170                 175                 180 ggc atg gcc cca atc cca gcc ggg cgg atg ggc atc cag cag cag cac       632
Gly Met Ala Pro Ile Pro Ala Gly Arg Met Gly Ile Gln Gln Gln His
                185                 190                 195 gcg gct ccc acg atg tcg tac caa gtg gca gcg ccg gcg ccc aac gcc       680
Ala Ala Pro Thr Met Ser Tyr Gln Val Ala Ala Pro Ala Pro Asn Ala
            200                 205                 210 gtg tac ccg gtt atg ggc aac ggc acg ggg tac cac aac ggg tac ccc       728
Val Tyr Pro Val Met Gly Asn Gly Thr Gly Tyr His Asn Gly Tyr Pro
        215                 220                 225 agg gcc atc gcg gtg gtg ccg ccg tct cag tgc gtg acg gcc gcc gtg       776
Arg Ala Ile Ala Val Val Pro Pro Ser Gln Cys Val Thr Ala Ala Val
    230                 235                 240 agc ccg ggg tcg tcg gac ggg gtg agc gcg atg acg cag gcg gag atg       824
Ser Pro Gly Ser Ser Asp Gly Val Ser Ala Met Thr Gln Ala Glu Met
245                 250                 255                 260 atg agc tgc att ggc aac gaa ggg gca ggg acg gtc cgg aac tac ggc       872
```

-continued

```
Met Ser Cys Ile Gly Asn Glu Gly Ala Gly Thr Val Arg Asn Tyr Gly
            265                 270                 275 ggc ggc ggc ggc ggc ggc agc gcg cgg aag cgc gac tcc ccc gag gac         920
Gly Gly Gly Gly Gly Gly Ser Ala Arg Lys Arg Asp Ser Pro Glu Asp
        280                 285                 290 gcg tgc acc gag aag acc gtg gag cgc cgg cag cgg cgg atg atc aag         968
Ala Cys Thr Glu Lys Thr Val Glu Arg Arg Gln Arg Arg Met Ile Lys
            295                 300                 305 aac cgt gag tcc gcg gcc cgg tca cgc gcc agg aag cag gcg tat acg        1016
Asn Arg Glu Ser Ala Ala Arg Ser Arg Ala Arg Lys Gln Ala Tyr Thr
        310                 315                 320 gtg gag ctc gaa gct gaa ctg aac cac ctc aaa gag gag aac gat cgc        1064
Val Glu Leu Glu Ala Glu Leu Asn His Leu Lys Glu Glu Asn Asp Arg
325                 330                 335                 340 ctc aga gca gag cag aag acg att ctg cta tcg aag aaa aag aag ctg        1112
Leu Arg Ala Glu Gln Lys Thr Ile Leu Leu Ser Lys Lys Lys Lys Leu
            345                 350                 355 gtg gag aag atg gtg gag cag gca agg gag aat gtg agc gcc aag aag        1160
Val Glu Lys Met Val Glu Gln Ala Arg Glu Asn Val Ser Ala Lys Lys
        360                 365                 370 ggc ggt cgc ggg ctg cgc cgc tcg ggc agc gcc atg tgg tgaactgtga         1209
Gly Gly Arg Gly Leu Arg Arg Ser Gly Ser Ala Met Trp
            375                 380                 385 cgactgacga gtgtctcgaa ttgtgcagtt ccagtccgct tgcttagttg cttgtatggg      1269
aaaaaaaatc ctgtacctgt cggtagcagc accgttagta acagtatgcc atgtggtcga      1329
cacaaacgtc tgcgagggac gatatggggc atgggcgaga gcttccgcgt tggcctgctg      1389
ctgttcatga gcctgggttg tacaaacaat aaagcaactg taagatagta gtaattaaac      1449
acaaagctct gtgttttcgt caaaaaaaaa aaaaaaaaaa aaaaaaaaaa aaaaaaaaaa      1509
a                                                                     1510
```

```
<210> SEQ ID NO 6
<211> LENGTH: 385
<212> TYPE: PRT
<213> ORGANISM: Zea mays

<400> SEQUENCE: 6

Met Ala Ser Glu Thr Thr Lys Asn Val Lys Ala Thr Leu Asp Glu Gln
1               5                   10                  15

Glu Val Thr Ser His Gln Arg Asp Gln Ser Ala Ala Glu Glu Glu Glu
            20                  25                  30

Val Val Val Val Asp Pro Leu Ala Arg Gln Ser Ser Val Met Ser
        35                  40                  45

Leu Thr Leu Glu Glu Leu Gln Ser Ser Leu Cys Glu Pro Gly Arg Asn
    50                  55                  60

Phe Gly Ser Met Asn Met Asp Glu Phe Met Ala Asn Ile Trp Asn Ala
65                  70                  75                  80

Glu Glu Phe Gln Ala Ala Thr Ala Thr Ala Thr Gly Gly Cys Ser Lys
                85                  90                  95

Gln Glu Gly Thr Gln Arg Glu Pro Met Met Pro Val Ala Asn Gly Thr
            100                 105                 110

Gly Glu Asn Gly Gly Leu Val Arg Gln Ala Asn Ala Ala Ala Gln Ala
        115                 120                 125

Val Val Gln Pro Gln Met Gly Ser Gly Gly Gly Gly Val Ala
    130                 135                 140

Ala Ser Gly Arg Gln Gln Val Thr Leu Ala Asp Met Thr Leu Glu Asp
```

```
                145                 150                 155                 160
Phe Leu Val Lys Ala Gly Val Val Arg Gly Ala Phe Ala Gly His Gly
                165                 170                 175
His Ala Val Val Gly Met Ala Pro Ile Pro Ala Gly Arg Met Gly Ile
            180                 185                 190
Gln Gln Gln His Ala Ala Pro Thr Met Ser Tyr Gln Val Ala Ala Pro
            195                 200                 205
Ala Pro Asn Ala Val Tyr Pro Val Met Gly Asn Gly Thr Gly Tyr His
        210                 215                 220
Asn Gly Tyr Pro Arg Ala Ile Ala Val Val Pro Pro Ser Gln Cys Val
225                 230                 235                 240
Thr Ala Ala Val Ser Pro Gly Ser Ser Asp Gly Val Ser Ala Met Thr
                245                 250                 255
Gln Ala Glu Met Met Ser Cys Ile Gly Asn Glu Gly Ala Gly Thr Val
                260                 265                 270
Arg Asn Tyr Gly Gly Gly Gly Gly Gly Ser Ala Arg Lys Arg Asp
            275                 280                 285
Ser Pro Glu Asp Ala Cys Thr Glu Lys Thr Val Glu Arg Arg Gln Arg
        290                 295                 300
Arg Met Ile Lys Asn Arg Glu Ser Ala Ala Arg Ser Arg Ala Arg Lys
305                 310                 315                 320
Gln Ala Tyr Thr Val Glu Leu Glu Ala Glu Leu Asn His Leu Lys Glu
                325                 330                 335
Glu Asn Asp Arg Leu Arg Ala Glu Gln Lys Thr Ile Leu Leu Ser Lys
            340                 345                 350
Lys Lys Lys Leu Val Glu Lys Met Val Glu Gln Ala Arg Glu Asn Val
            355                 360                 365
Ser Ala Lys Lys Gly Gly Arg Gly Leu Arg Arg Ser Gly Ser Ala Met
        370                 375                 380
Trp
385

<210> SEQ ID NO 7
<211> LENGTH: 19
<212> TYPE: DNA
<213> ORGANISM: Zea mays

<400> SEQUENCE: 7
gaagtccacg tggaggtgg                                                19

<210> SEQ ID NO 8
<211> LENGTH: 30
<212> TYPE: DNA
<213> ORGANISM: Zea mays

<400> SEQUENCE: 8
gactagttct agatcgcgag cggccgccct                                    30

<210> SEQ ID NO 9
<211> LENGTH: 20
<212> TYPE: DNA
<213> ORGANISM: Artificial sequence
<220> FEATURE:
<223> OTHER INFORMATION: Synthetically derived primer

<400> SEQUENCE: 9
gcgacagcga cgacagatca                                               20
```

<210> SEQ ID NO 10
<211> LENGTH: 20
<212> TYPE: DNA
<213> ORGANISM: Artificial sequence
<220> FEATURE:
<223> OTHER INFORMATION: Synthetically derived primer

<400> SEQUENCE: 10
agcgccagaa gcggaggcca                                               20

<210> SEQ ID NO 11
<211> LENGTH: 21
<212> TYPE: DNA
<213> ORGANISM: Artificial sequence
<220> FEATURE:
<223> OTHER INFORMATION: Synthetically derived primer

<400> SEQUENCE: 11
ccttcaccag gaagtcctcc a                                             21

<210> SEQ ID NO 12
<211> LENGTH: 20
<212> TYPE: DNA
<213> ORGANISM: Artificial sequence
<220> FEATURE:
<223> OTHER INFORMATION: Synthetically derived primer

<400> SEQUENCE: 12
ggccacgcgt cgactagtac                                               20

<210> SEQ ID NO 13
<211> LENGTH: 20
<212> TYPE: DNA
<213> ORGANISM: Artificial sequence
<220> FEATURE:
<223> OTHER INFORMATION: Synthetically derived primer

<400> SEQUENCE: 13
aggaactcct ccagagtcat                                               20

<210> SEQ ID NO 14
<211> LENGTH: 21
<212> TYPE: DNA
<213> ORGANISM: Artificial sequence
<220> FEATURE:
<223> OTHER INFORMATION: Synthetically derived primer

<400> SEQUENCE: 14
tcgtcgaacg tcaacgagta g                                             21

<210> SEQ ID NO 15
<211> LENGTH: 21
<212> TYPE: DNA
<213> ORGANISM: Artificial sequence
<220> FEATURE:
<223> OTHER INFORMATION: Synthetically derived primer

<400> SEQUENCE: 15
aaccaatcct ccgttctcac c                                             21

<210> SEQ ID NO 16
<211> LENGTH: 16
<212> TYPE: DNA
<213> ORGANISM: Zea mays

<400> SEQUENCE: 16

```
tcgacccacg cgtccg                                              16

<210> SEQ ID NO 17
<211> LENGTH: 12
<212> TYPE: DNA
<213> ORGANISM: Zea mays

<400> SEQUENCE: 17
gggtgcgcag gc                                                  12

<210> SEQ ID NO 18
<211> LENGTH: 19
<212> TYPE: DNA
<213> ORGANISM: Artificial sequence
<220> FEATURE:
<223> OTHER INFORMATION: Synthetically derived primer

<400> SEQUENCE: 18
gaagtccacg tggaggtgg                                           19

<210> SEQ ID NO 19
<211> LENGTH: 19
<212> TYPE: DNA
<213> ORGANISM: Artificial sequence
<220> FEATURE:
<223> OTHER INFORMATION: Synthetically derived primer

<400> SEQUENCE: 19
tcccacctcc acgtggact                                           19

<210> SEQ ID NO 20
<211> LENGTH: 19
<212> TYPE: DNA
<213> ORGANISM: Artificial sequence
<220> FEATURE:
<223> OTHER INFORMATION: Synthetically derived primer

<400> SEQUENCE: 20
gaagtaacat gttcggtgg                                           19

<210> SEQ ID NO 21
<211> LENGTH: 19
<212> TYPE: DNA
<213> ORGANISM: Artificial sequence
<220> FEATURE:
<223> OTHER INFORMATION: Synthetically derived primer

<400> SEQUENCE: 21
tcccaccgaa catgttact                                           19

<210> SEQ ID NO 22
<211> LENGTH: 21
<212> TYPE: DNA
<213> ORGANISM: Zea mays

<400> SEQUENCE: 22
caccttctac aacgagctcc g                                        21

<210> SEQ ID NO 23
<211> LENGTH: 21
<212> TYPE: DNA
<213> ORGANISM: Zea mays

<400> SEQUENCE: 23
```
taatcaaggg caacgtaggc a                    21

<210> SEQ ID NO 24
<211> LENGTH: 20
<212> TYPE: DNA
<213> ORGANISM: Artificial sequence
<220> FEATURE:
<223> OTHER INFORMATION: Synthetically derived primer

<400> SEQUENCE: 24
tgatctgtcg tcgctgtcgc                      20

<210> SEQ ID NO 25
<211> LENGTH: 21
<212> TYPE: DNA
<213> ORGANISM: Artificial sequence
<220> FEATURE:
<223> OTHER INFORMATION: Synthetically derived primer

<400> SEQUENCE: 25
actccaggtt acttgcatta t                    21

<210> SEQ ID NO 26
<211> LENGTH: 20
<212> TYPE: DNA
<213> ORGANISM: Artificial sequence
<220> FEATURE:
<223> OTHER INFORMATION: Synthetically derived primer

<400> SEQUENCE: 26
tcggttattc ccaatacaca                      20

<210> SEQ ID NO 27
<211> LENGTH: 20
<212> TYPE: DNA
<213> ORGANISM: Artificial sequence
<220> FEATURE:
<223> OTHER INFORMATION: Synthetically derived primer

<400> SEQUENCE: 27
agcagcggtg aaccagcttg                      20

<210> SEQ ID NO 28
<211> LENGTH: 21
<212> TYPE: DNA
<213> ORGANISM: Artificial sequence
<220> FEATURE:
<223> OTHER INFORMATION: Synthetically derived primer

<400> SEQUENCE: 28
catgacgctg gaggacttcc t                    21

<210> SEQ ID NO 29
<211> LENGTH: 18
<212> TYPE: DNA
<213> ORGANISM: Artificial sequence
<220> FEATURE:
<223> OTHER INFORMATION: Synthetically derived primer

<400> SEQUENCE: 29
ttgacgaaaa cacagagc                        18

<210> SEQ ID NO 30
<211> LENGTH: 20
<212> TYPE: DNA
<213> ORGANISM: Artificial sequence

```
-continued
<220> FEATURE:
<223> OTHER INFORMATION: Synthetically derived primer

<400> SEQUENCE: 30
tctgccgaca gtggtcccaa                                                    20
```